(12) United States Patent
Andanayya et al.

(10) Patent No.: US 11,298,360 B2
(45) Date of Patent: Apr. 12, 2022

(54) OPHTHALMIC COMPOSITIONS OF BRINZOLAMIDE

(71) Applicant: SHILPA MEDICARE LIMITED, Raichur (IN)

(72) Inventors: Saraganachari Andanayya, Bangalore (IN); Narayanaswamy Abhilash, Bangalore (IN); Sreenivasa Reddy, Bangalore (IN); Shivakumar Pradeep, Vizianagaram (IN)

(73) Assignee: SHILPA MEDICARE LIMITED

( * ) Notice: Subject to any disclaimer, the term of this patent is extended or adjusted under 35 U.S.C. 154(b) by 0 days.

(21) Appl. No.: 16/470,987

(22) PCT Filed: Apr. 2, 2019

(86) PCT No.: PCT/IB2019/052677
§ 371 (c)(1),
(2) Date: Jun. 19, 2019

(87) PCT Pub. No.: WO2019/207380
PCT Pub. Date: Oct. 31, 2019

(65) Prior Publication Data
US 2021/0353635 A1    Nov. 18, 2021

(30) Foreign Application Priority Data
Apr. 25, 2018 (IN) .............................. 201841015643

(51) Int. Cl.
| | | |
|---|---|---|
| *A61K 31/542* | (2006.01) |
| *A61K 47/40* | (2006.01) |
| *A61K 47/02* | (2006.01) |
| *A61K 47/10* | (2017.01) |
| *A61K 47/32* | (2006.01) |
| *A61P 27/02* | (2006.01) |

(52) U.S. Cl.
CPC ............ *A61K 31/542* (2013.01); *A61K 47/02* (2013.01); *A61K 47/10* (2013.01); *A61K 47/32* (2013.01); *A61K 47/40* (2013.01); *A61P 27/02* (2018.01)

(58) Field of Classification Search
CPC ...... A61K 31/542; A61K 47/02; A61K 47/10; A61K 47/32; A61K 47/40; A61P 27/02
USPC ....................................................... 514/224.2
See application file for complete search history.

(56) References Cited

U.S. PATENT DOCUMENTS

| | | |
|---|---|---|
| 5,378,703 A | 1/1995 | Dean et al. |
| 6,071,904 A | 6/2000 | Ali et al. |
| 2016/0339105 A1 | 11/2016 | Mandar et al. |

FOREIGN PATENT DOCUMENTS

| | | | |
|---|---|---|---|
| EP | 0941094 B1 | 12/2001 | |
| EP | 0527801 B1 | 7/2002 | |
| WO | 1998025620 A1 | 6/1998 | |
| WO | 2013090842 A2 | 6/2013 | |
| WO | WO-2013114397 A2 * | 8/2013 | ........... C07D 513/04 |

* cited by examiner

*Primary Examiner* — Kristin A Vajda

(57) ABSTRACT

The present invention relates to an aqueous ophthalmic solution for treatment of elevated intraocular pressure in patients with ocular hypertension or open-angle glaucoma, the solution comprising at least 0.5 w/v % brinzolamide dissolved in the solution; hydroxy-propyl-β-cyclodextrin; polyvinyl caprolactam-polyvinyl acetate-polyethylene glycol graft copolymer; and water and/or the process for preparation thereof.

10 Claims, 1 Drawing Sheet

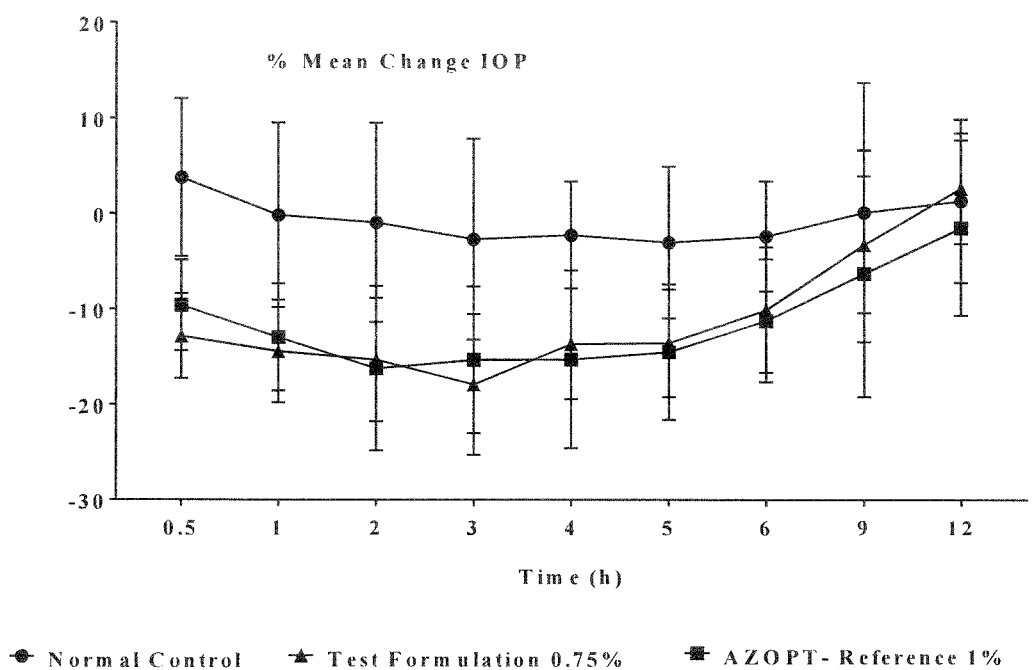

OPHTHALMIC COMPOSITIONS OF BRINZOLAMIDE

FIELD OF THE INVENTION

The present invention provides an ophthalmic composition which is an aqueous solution. It relates more specifically an eye drop containing brinzolamide.

BACKGROUND OF THE INVENTION

Brinzolamide is a carbonic anhydrase inhibitor used to lower intraocular pressure in patients with ocular hypertension or open-angle glaucoma. Brinzolamide is chemically (R)-(+)-4-ethylamino-2-(3-methoxypropyl)-3,4-dihydro-2H-thieno[3,2-e]-1,2-thiazine-6-sulfonamide-1,1-dioxide and has the empirical formula $C_{12}H_{21}N_3O_5S_3$. Brinzolamide has a molecular weight of 383.5 and a melting point of about 131° C.

This compound is disclosed in U.S. Pat. No. 5,378,703 (Dean, et al.). The compound is also disclosed in European patent EP 527801. U.S. Pat. No. 6,071,904 discloses processes for preparation of brinzolamide ophthalmic composition.

Brinzolamide in the form of ophthalmic suspension is developed and marketed by Alcon Laboratories Inc. in United States under the brand name Azopt® (brinzolamide ophthalmic suspension 1%). Brinzolamide is indicated for lowering elevated intraocular pressure (IOP) in patients with open-angle glaucoma or ocular hypertension (OHT).

Various methods have been disclosed in the prior art for the preparation of brinzolamide ophthalmic suspension. International patent application WO 98/25620 teaches that conventional sterilization methods cannot be employed in the manufacture of suspensions comprising brinzolamide since the compound recrystallizes as large needle-shaped crystals, upon cooling, after autoclaving.

According to WO 98/25620, dry heat sterilization is also not suitable, since it causes melting of the material, whereas sterilization by ethylene oxide and gamma irradiation introduces unacceptable degradation products.

EP0941094 discloses a process for making brinzolamide suspension by autoclaving of concentrated slurry of brinzolamide and tyloxapol; or brinzolamide and Triton X in milling bottle, and ball milling of the hot slurry after autoclaving, and then adding the slurry to the rest of the ingredients. It should be noted here that high temperatures and pressures of autoclave will dissolve brinzolamide. Later, when autoclaving is complete, upon cooling brinzolamide precipitates as large shaped crystals, having particle size of 1000 to 5000 μm. However, inclusion of tyloxapol and/or Triton X in the slurry allows the crystals to break up easily by ball milling. Brinzolamide cannot be administered as these large needle shaped crystals, as they will damage the eyes. Hence, precipitated brinzolamide crystals need to be milled to reduce their particle size.

According to US20160339105, the sterile aqueous formulation of a carbonic anhydrase inhibitor such as brinzolamide in combination with polymers like Soluplus® and a surfactant like polysorbate 80, as well as methods of preparation thereof, is disclosed.

WO2013090842, discloses the ophthalmic composition comprising cyclodextrins for enhancing the solubility of drugs and Soluplus as the polymer for enhancing the stability of the ophthalmic composition.

However, there exists a need to provides an ophthalmic composition which is an aqueous solution. It relates more specifically an eye drop containing brinzolamide.

OBJECTS OF THE INVENTION

In one object, the present invention provides an ophthalmic composition which is an aqueous solution containing brinzolamide.

In another object, the present invention provides an ophthalmic solution composition which is an aqueous solution comprising brinzolamide, solubilizing agents, isotonizing agents, chelating agent, buffering agent and purified water.

In yet another object, the present invention provides an ophthalmic solution composition which is an aqueous solution comprising brinzolamide, solubilizing agents, isotonizing agents, chelating agent, viscosity enhancing polymer, buffering agent and purified water.

BRIEF DESCRIPTION OF THE DRAWINGS

FIG. 1: discloses the comparison of percentage mean change in intraocular pressure of normal control, example-7 (0.75% brinzolamide ophthalmic solution) and Azopt® brinzolamide 1.0% ophthalmic suspension.

SUMMARY OF THE INVENTION

The present invention provides an aqueous ophthalmic solution for treatment of elevated intraocular pressure in patients with ocular hypertension or open-angle glaucoma, the solution comprising at least 0.5 w/v % brinzolamide.

In embodiments of the invention, the present invention provides an aqueous ophthalmic solution for treatment of elevated intraocular pressure in patients with ocular hypertension or open-angle glaucoma, the solution comprising at least 0.5 w/v % brinzolamide but no greater than 0.95 w/v % of brinzolamide dissolved in the solution.

In another embodiment, the present invention provides an aqueous ophthalmic solution for treatment of elevated intraocular pressure in patients with ocular hypertension or open-angle glaucoma, the solution comprising at least 0.5 w/v % brinzolamide dissolved in the solution, hydroxypropyl-β-cyclodextrin; polyvinyl caprolactam-polyvinyl acetate-polyethylene glycol graft copolymer; and water.

In further embodiments of the invention, the present invention provides an aqueous ophthalmic solution comprising at least 0.5 w/v % brinzolamide but no greater than 0.95 w/v % of brinzolamide dissolved in the solution; at least 1.0 w/v % but no greater than 10.0 w/v % cyclodextrin derivative selected from group consisting of hydroxy-propyl-β-cyclodextrin, hydroxy-propyl-γ-cyclodextrin, sulfobutyl-ether-β-cyclodextrin and combinations thereof; about 0.2 w/v % to about 4.0 w/v % polyvinyl caprolactam-polyvinyl acetate-polyethylene glycol graft copolymer; about 0.1 w/v % to about 1.0 w/v % sodium chloride and water.

In specific embodiment of the invention, the present invention provides an aqueous ophthalmic solution comprising of about 0.75 w/v % brinzolamide dissolved in the solution; of about 5.0 w/v % hydroxy-propyl-β-cyclodextrin; about 1.0 w/v % polyvinyl caprolactam-polyvinyl acetate-polyethylene glycol graft copolymer; about 0.7 w/v % sodium chloride and water.

DETAILED DESCRIPTION OF THE INVENTION

The present invention relates to an ophthalmic composition for treatment of elevated intraocular pressure in patients with ocular hypertension or open-angle glaucoma.

In one object, the present invention provides an ophthalmic composition which is an aqueous solution containing brinzolamide.

In a preferred embodiment, the pharmaceutical composition of the invention is ophthalmic solution.

In the most preferred embodiment, the pharmaceutical ophthalmic solution composition comprising brinzolamide and pharmaceutically acceptable excipients. In a preferred embodiment, the ophthalmic composition is a single dose or multi-dose ophthalmic composition.

Unless otherwise indicated, all the component amounts (i.e. concentrations) are presented on a weight volume percent (w/v %) basis and all references to concentrations of brinzolamide free base.

Brinzolamide is preferably used in a pharmaceutical ophthalmic solution composition of at least 0.5 w/v %, more typically at least 0.55 w/v %, even more typically at least 0.6 w/v % or 0.65 w/v %, still more typically at least 0.7 w/v %, possibly at least 0.75 w/v % and even possibly at least 0.8 w/v % or 0.85 w/v % but typically no greater than 0.95 w/v %, still more typically no greater than 0.9 w/v %, still most typically no greater than 0.8 w/v % and even possibly no greater than 0.78 w/v %. The concentration of 0.75 w/v % is more important, as at the concentration of 0.75 w/v % of brinzolamide as per the present invention has the same equivalent efficacy in treatment of elevated intraocular pressure in patients with ocular hypertension or open-angle glaucoma in comparison to that of the 1.0% ophthalmic suspension of brinzolamide.

In embodiments of the invention the present invention provides an aqueous ophthalmic solution for treatment of elevated intraocular pressure in patients with ocular hypertension or open-angle glaucoma, the solution comprising at least 0.5 w/v % brinzolamide.

In further embodiments of the invention the present invention provides an aqueous ophthalmic solution for treatment of elevated intraocular pressure in patients with ocular hypertension or open-angle glaucoma, the solution comprising at least 0.5 w/v % brinzolamide but no greater than 0.95 w/v % of brinzolamide dissolved in the solution.

In specific embodiments of the invention the present invention provides an aqueous ophthalmic solution for treatment of elevated intraocular pressure in patients with ocular hypertension or open-angle glaucoma, the solution comprising of about 0.75 w/v % of brinzolamide.

Generally, it is preferred that the entire concentration of brinzolamide is dissolved in the composition as a water based or aqueous solution. However, it is contemplated that a small portion of brinzolamide could be only partially suspended. For example, a major portion of brinzolamide could be in solution with about less than 5% by weight of drug could be in suspended form.

In another embodiment, the present invention provides an ophthalmic solution composition which is an aqueous solution comprising brinzolamide, solubilizing agents, isotonizing agents, chelating agent, viscosity enhancing polymer, buffering agent and purified water.

In a further embodiment, the present invention provides an ophthalmic solution composition which is an aqueous solution comprising brinzolamide, solubilizing agents, isotonizing agents, chelating agent, optional viscosity enhancing polymer, optional buffering agent and purified water.

In another embodiment, the brinzolamide pharmaceutical ophthalmic solution of the present invention is characterized the ophthalmic solution contains at least 0.5 w/v % brinzolamide but no greater than 0.95 w/v % of brinzolamide dissolved in the solution; about 1.0 w/v % to about 15.0 w/v % solubilizing agents; about 0.1 w/v % to about 3.0 w/v % isotonizing agent; about 0.01 w/v % to about 0.4 w/v % chelating agent and water.

In yet another embodiment, the brinzolamide pharmaceutical ophthalmic solution of the present invention is characterized the ophthalmic solution contains at least 0.5 w/v % brinzolamide but no greater than 0.95 w/v % of brinzolamide dissolved in the solution; about 1.0 w/v % to about 15.0 w/v % solubilizing agents; about 0.01 w/v % to about 5.0 w/v % viscosity enhancing polymer; about 0.1 w/v % to about 3.0 w/v % isotonizing agent; about 0.01 w/v % to about 0.4 w/v % chelating agent and water.

Examples of the solubilizing agent is selected form the group consisting of α-cyclodextrin; β-cyclodextrin; γ-cyclodextrin; cyclodextrin derivatives such as ether and mixed ether derivatives and those derivatives bearing sugar residues such as hydroxyethyl, hydroxypropyl (including 2- and 3-hydroxypropyl) and dihydroxypropyl ethers, their corresponding mixed ethers and further mixed ethers with methyl or ethyl groups, such as methyl-hydroxyethyl, ethyl-hydroxyethyl and ethyl-hydroxypropyl ethers of α-, β- and γ-cyclodextrin; maltosyl, glucosyl and maltotriosyl derivatives of β- and γ-cyclodextrin, which may contain one or more sugar residues, e.g. glucosyl or diglucosyl, maltosyl or dimaltosyl, as well as various mixtures thereof, e.g. a mixture of maltosyl and dimaltosyl derivatives; cyclodextrin derivatives comprising anionic functional groups such as sulfobutylether derivatives, sulfonates, phosphates, and the like, such as hydroxypropyl-β-cyclodextrin, hydroxypropyl-γ-cyclodextrin, sulfobutylether-β-cyclodextrin, and sulfobutylether-γ-cyclodextrin, as well as hydroxyethyl-β-cyclodextrin, hydroxyethyl-γ-cyclodextrin, dihydroxypropyl-β-cyclodextrin, glucosyl-β-cyclodextrin, diglucosyl-β-cyclodextrin, maltosyl-β-cyclodextrin, maltosyl-γ-cyclodextrin, maltotriosyl-β-cyclodextrin, maltotriosyl-γ-cyclodextrin and dimaltosyl-β-cyclodextrin; polyvinyl caprolactam-polyvinyl acetate-polyethylene glycol graft copolymer (SOLUPLUS®) and/or combination thereof. Preferably, the solubilizing agents used in the present composition is hydroxy-propyl-β-cyclodextrin and polyvinyl caprolactam-polyvinyl acetate-polyethylene glycol graft copolymer (SOLUPLUS®). Cyclodextrin derivatives used in the pharmaceutical ophthalmic solution composition is of about 1.0 w/v % to about 10.0 w/v %; more preferably of about at least 2.0 w/v % but no greater than 10.0 w/v %; even more preferably of about 2.5 w/v % to about 10 w/v % and most preferably of about 5.0 w/v %. Caprolactam-polyvinyl acetate-polyethylene glycol graft copolymer is preferably used at a concentration of about 0.01 w/v % to about 5.0 w/v %; more preferably at a concentration of about 0.2 w/v % to about 4.0 w/v % and most preferably at a concentration of about 1.0 w/v %.

Examples of the isotonizing agents present in the present ophthalmic composition are preferably at least one type selected form the group consisting of sodium chloride, potassium chloride, and concentrated glycerine. In the present ophthalmic composition, the preferable isotonizing agent used is sodium chloride or glycerine. The isotonizing agent is preferable used at a concentration of about 0.1 w/v % to about 3 w/v %; more preferably of about 0.3 w/v % to about 2.0 w/v % and most preferably at a concentration of about 0.7 w/v %.

In accordance with this invention, the pH is adjusted to about 6.0 to about 7.8 in order to secure a useful shelf life. The maximum stability of the ophthalmic solution of brinzolamide is achieved when the pH is maintained at a pH of about 7.5. The pH of the solution is adjusted with the hydrochloric acid or sodium hydroxide. The compositions will have an osmolality of 200 to 400 or 450 milliosmoles per kilogram (mOsm/kg), more preferably 240 to 360 mOsm/kg.

Examples of the chelating agent in the present ophthalmic composition is preferably at least one type selected from the group consisting of edetic acid, ethylenediaminetetraacetic acid (EDTA), citric acid, metaphosphoric acid, pyrophosphoric acid, polyphosphoric acid, malic acid, tartaric acid, phytic acid, and/or combination thereof. Preferably, the chelating agent is selected from EDTA. Chelating agent preferably used in the pharmaceutical ophthalmic solution composition of about 0.01% to about 0.4% based on the total weight of the composition. Most preferably, chelating agent used in the composition of about 0.05% to about 0.3% based on total weight of the composition.

Examples of the buffering agent selected from the group consisting of diethanolamine, triethanolamine, sodium hydroxide, phosphate buffer, histidine buffer, hydrochloric acid, sodium citrate dihydrate, citric acid and mono basic sodium phosphate. Buffering agent preferably used in the pharmaceutical injection composition of sufficient quantity.

In embodiments of the invention, the ophthalmic composition further comprise viscosity enhancing polymer selected form the group consisting of hydroxypropyl methyl cellulose, hydroxy propyl cellulose, carbomer, polyvinyl alcohol, xyloglucan carrageenan, and/or combination thereof.

In embodiments of the invention the present invention provides an aqueous ophthalmic solution comprising at least 0.5 w/v % brinzolamide but no greater than 0.95 w/v % of brinzolamide dissolved in the solution; at least 1.0 w/v % but no greater than 10.0 w/v % cyclodextrin derivative selected from group consisting of hydroxy-propyl-β-cyclodextrin, hydroxy-propyl-γ-cyclodextrin, sulfobutyl-ether-β-cyclodextrin and combinations thereof; about 0.2 w/v % to about 5.0 w/v % polyvinyl caprolactam-polyvinyl acetate-polyethylene glycol graft copolymer; about 0.1 w/v % to about 1.0 w/v % sodium chloride and water.

In another embodiments of the invention the present invention provides an aqueous ophthalmic solution consisting essentially of at least 0.5 w/v % brinzolamide but no greater than 0.95 w/v % of brinzolamide dissolved in the solution; at least 1.0 w/v % but no greater than 10.0 w/v % cyclodextrin derivative selected from group consisting of hydroxy-propyl-β-cyclodextrin, hydroxy-propyl-γ-cyclodextrin, sulfobutyl-ether-β-cyclodextrin and combinations thereof; about 0.2 w/v % to about 5.0 w/v % polyvinyl caprolactam-polyvinyl acetate-polyethylene glycol graft copolymer; about 0.1 w/v % to about 1.0 w/v % sodium chloride and water.

In embodiments of the invention the present invention provides an aqueous ophthalmic solution comprising of about 0.75 w/v % brinzolamide dissolved in the solution; of about 5.0 w/v % hydroxy-propyl-β-cyclodextrin; about 1.0 w/v % polyvinyl caprolactam-polyvinyl acetate-polyethylene glycol graft copolymer; about 0.7 w/v % sodium chloride and water.

In a further embodiment of the invention the present invention provides an aqueous ophthalmic solution consisting essentially of about 0.75 w/v % brinzolamide dissolved in the solution; of about 5.0 w/v % hydroxy-propyl-β-cyclodextrin; about LO w/v % polyvinyl caprolactam-polyvinyl acetate-polyethylene glycol graft copolymer; about 0.7 w/v % sodium chloride and water.

It is generally preferred that the composition of the present invention be provided in an eye dropper that is configured to dispense the composition as eye drops topically to the eye. However, desired size of a single eye drop (i.e., droplet size) for the ophthalmic composition can be difficult to accomplish. Desired droplet size is typically at least 10 µl, more typically at least 18 µl and even more typically at least 23 µl, most typically 50 µl, even most typically 37 µl, but is typically no greater than 60 µl.

The compositions of the present invention are packed in preservative-free containers like blow-fill seal (BFS) single-dose droppers and Aptar® ophthalmic squeeze dispensers.

The following example is provided to illustrate the present invention. It is understood, however, that the invention is not limited to the specific conditions or details described in the example below. The example should not be construed as limiting the invention as the examples merely provide specific methodology useful in the understanding and practice of the invention and its various aspects. While certain preferred and alternative embodiments of the invention have been set forth for purposes of disclosing the invention, modification to the disclosed embodiments can occur to those who are skilled in the art.

Example 1 to 4

Ophthalmic solution with the following compositions are prepared.

| | Compositions | | | |
|---|---|---|---|---|
| Ingredients | Example 1 (w/v %) | Example 2 (w/v %) | Example 3 (w/v %) | Example 4 (w/v %) |
| Brinzolamide | 0.5% | 0.5% | 0.5% | 0.5% |
| Hydroxypropyl beta cyclodextrin | 0.5%-12.5% | 0.5%-12.5% | 0.5%-12.5% | 0.5%-12.5% |
| Soluplus ® | 0.5%-2.5% | 0.5%-2.5% | 0.5%-2.5% | 0.5%-2.5% |
| Glycerin | — | 0.1-3% | — | 0.1-3% |
| Sodium Chloride | 0.1-3% | — | 0.1-3% | — |
| Edetate disodium dihydrate | 0.01%-0.4% | 0.01%-0.4% | 0.01%-0.4% | 0.01%-0.4% |
| Viscosity enhancing Polymer | — | — | 0.01%-1% | 0.01%-1% |
| Hydrochloric acid/ Sodium Hydroxide | q.s to pH 7.5 | q.s to pH 7.5 | q.s to pH 7.5 | q.s to pH 7.5 |
| Purified Water | q.s to 100% | q.s to 100% | q.s to 100% | q.s to 100% |

Ophthalmic solution is prepared as follows:
Manufacturing Procedure for Formulations of Example 1 & Example 2
 Collect 120% batch size of purified water in a clean and dry vessel and subjected for nitrogen purging.
 Collect 80% batch size of purified water in a suitable manufacturing vessel.
 Add dispensed quantity of Hydroxypropyl beta cyclodextrin and stir for 10 minutes.

Add dispensed quantity of Soluplus and stir for 15 minutes.
Heat the above bulk solution to 70° C.
Add dispensed quantity of Brinzolamide and stir for 15 minutes.
Allow the bulk solution to cool to room temperature
Add dispensed quantity of Glycerin/Sodium Chloride and stir for 10 minutes.
Add dispensed quantity of Edetate disodium dihydrate and stir for 10 minutes.
Adjust the pH to 7.5 with freshly prepared Hydrochloric acid/Sodium hydroxide solution of suitable normality.
Make up the volume up to 100% batch size with purified water and stir for 0 minutes.
Filter the bulk solution through 0.22μ filter.
Fill the bulk solution into suitable containers, label and store.

Manufacturing Procedure for Formulations of Example 3 & Example 4

Collect 120% batch size of purified water in a clean and dry vessel and subjected for nitrogen purging.
Preparation of Polymer Phase:
Collect 30% batch size of purified water in a suitable manufacturing vessel.
Add dispensed quantity of Viscosity enhancing polymer and stir till the polymer is completely wet.
Heat the solution if required.
Make up the volume of the polymer phase to 35% batch size with purified water.
Subject the polymer phase for sterilization by autoclaving at 121° C. for 15 minutes.
Preparation of API Phase:
Collect 40% batch size of purified water from step 1.0 in a suitable manufacturing vessel.
Add dispensed quantity of Hydroxypropyl beta cyclodextrin and stir for 10 minutes.
Add dispensed quantity of Soluplus and stir for 15 minutes.
Heat the above bulk solution to 70° C.
Add dispensed quantity of Brinzolamide and stir for 15 minutes.
Allow the bulk solution to cool to room temperature.
Add dispensed quantity of Glycerin/Sodium chloride and stir for 10 minutes.
Add dispensed quantity of Edetate disodium dihydrate and stir for 10 minutes.
Make up the volume of the API phase to 60% batch size with purified water.
Filter the API phase through 0.22μ filter.
Mixing of polymer phase and API phase:
Add the API phase to polymer phase and stir for 15 minutes.
Check and adjust the pH to 7.5 with freshly prepared Hydrochloric acid/Sodium hydroxide solution of suitable normality.
Make up the volume up to 100% batch size with purified water and stir for 10 minutes.
Fill the bulk solution into suitable containers, label and store.

Example 5 to 7

| Ingredients | Example 5 % w/v | Example 6 % w/v | Example 7 % w/v |
|---|---|---|---|
| Brinzolamide | 0.75 | 0.75 | 0.75 |
| Hydroxy-propyl-β-cyclodextrin | 5.0 | 5.0 | 5.0 |
| Polyvinyl caprolactam-polyvinyl acetate-polyethylene glycol graft copolymer (Soluplus ®) | 1.0 | 1.0 | 1.0 |
| Sodium Chloride | 0.7 | 0.7 | 0.7 |
| Disodium EDTA | 0.1 | 0.1 | 0.1 |
| Hydrochloric acid/Sodium hydroxide | q.s to pH 5 | q.s to pH 6.8 | q.s to pH 7.5 |
| Purified water | q.s to 100% | q.s to 100% | q.s to 100% |

Process for Preparation:
1. Collect 120% batch size of purified water in a clean and dry vessel and subjected for nitrogen purging
2. Retain 80% batch size of purified water in a suitable manufacturing vessel.
3. Add dispensed quantity of Hydroxy-propyl-β-cyclodextrin and stir for 10 minutes.
4. Add dispensed quantity of Soluplus® and stir for 15 minutes.
5. Heat the above bulk solution to 70° C.
6. Add dispensed quantity of Brinzolamide and stir for 15 mins.
7. Allow the bulk solution to cool to room temperature.
8. Add dispensed quantity of Sodium chloride and stir for 10 mins.
9. Add dispensed quantity of Disodium EDTA and stir for 10 mins.
10. Check and adjust the required pH (as above) with freshly prepared Hcl/NaOH solution of suitable normality.
11. Make up the volume up to 100% batch size with purified water from step 1.0 and stir for 10 mins.
12. Fill the bulk solution into suitable containers and label and store.

Example-8: Stability Studies

The compositions of example 5, 6 and 7 are stored at 40° C./75% RH and was tested for impurities at specific intervals. The results of examples 5, 6 and 7 are tabulated in tables 1, 2 and 3 respectively.

TABLE 1

| Time | Assay | pH | Osmolality (mOsmol/kg) | Imp B | Single Major unknown Imp | Total Impurity |
|---|---|---|---|---|---|---|
| Initial | 102.3 | 5.0 | 280 | 0.03 | 0.02 | 0.06 |
| 1 M | 96.5 | 4.8 | 265 | 0.32 | 0.04 | 0.54 |
| 2 M | 95.0 | 4.72 | 240 | 0.48 | 0.09 | 1.42 |
| 3 M | 94.5 | 4.8 | 220 | 0.92 | 0.12 | 3.48 |
| 6 M | 94.0 | 4.65 | 200 | 1.9 | 1.2 | 5.25 |

TABLE 2

| Time | Assay | pH | Osmolality (mOsmol/kg) | Imp B | Single Major unknown Imp | Total Impurity |
|---|---|---|---|---|---|---|
| Initial | 99.3 | 6.8 | 285 | 0.03 | 0.01 | 0.04 |
| 1 M | 98.5 | 6.5 | 289 | 0.13 | 0.04 | 0.25 |
| 2 M | 99.4 | 6.32 | 300 | 0.17 | 0.05 | 0.35 |
| 3 M | 99.2 | 6.46 | 320 | 0.18 | 0.07 | 0.39 |
| 6 M | 98.5 | 6.85 | 330 | 0.44 | 0.17 | 0.94 |

TABLE 3

| Time | Assay | pH | Osmolality (mOsmol/kg) | Imp B | Single Major unknown Imp | Total Impurity |
|---|---|---|---|---|---|---|
| Initial | 99.9 | 7.5 | 279 | ND | 0.01 | 0.01 |
| 1 M | 102.3 | 7.37 | 289 | 0.04 | 0.02 | 0.06 |
| 2 M | 103.2 | 7.27 | 290 | 0.06 | 0.03 | 0.16 |
| 3 M | 105.3 | 7.11 | 301 | 0.08 | 0.05 | 0.23 |
| 6 M | 102.0 | 7.32 | 335 | 0.14 | 0.12 | 0.32 |

From the above stability studies, it is found that the compositions with pH of about 6.8 and about 7.5 are found to be stable with total impurities of less than 2.0% whereas the composition with pH of about 5.0 is less stable and have the impurities of more than 4.0%.

Example 9: Pre-Clinical Efficacy Study

The efficacy of the example-7 formulation comprising 0.75 w/v % of brinzolamide solution was compared with 1.0 w/v % Azopt® Brinzolamide ophthalmic suspension for the treatment of intraocular pressure (IOP) in male New Zealand white rabbits.

The animals were categorized into three groups assigned with five animals in each. The animals of the group G1 were considered as control group animals. The animals of the group G2 were instilled with example 7 formulation (Brinzolamide ophthalmic solution 0.75%) one time a day and the animals of the group G3 were instilled with reference formulation (Azopt®—Brinzolamide ophthalmic suspension 1%) one time a day.

After acclimatization of animals to experimental room conditions, intra ocular pressure (IOP) was measured using a rebound Tonometer for 15 male New Zealand White Rabbits and this was considered as baseline reading. After IOP reading, animals were randomized, based on baseline IOP and equally allotted to 3 groups with 5 animals in each group.

After animal allocation to groups animals of the group G2 were instilled with the example 7 formulation and animals of group G3 were instilled with the Azopt® 1.0% brinzolamide ophthalmic suspension and IOP measurements were made at 0 min, 0.5 h, 1 h, 2 h, 3 h, 4 h, 5 h, 6 h, 9 h and 12 hours. IOP were measured for both the eyes and the Percentage mean IOP of all the three groups is disclosed in Table-4 and FIG. 1.

TABLE 4

| Time point (h) | Normal Control | Test formulation | Reference |
|---|---|---|---|
| 0.5 | 3.77 ± 2.62 | −12.8 ± 1.40**** | −9.62 ± 1.50** |
| 1 | −0.16 ± .06 | −14.39 ± 1.70*** | −12.95 ± 1.77* |
| 2 | −0.94 ± 3.30 | −15.3 ± 2.05*** | −16.22 ± 2.72** |
| 3 | −2.7 ± 3.33 | −17.88 ± 2.33*** | −15.32 ± 2.43* |
| 4 | −2.24 ± 1.77 | −13.64 ± 1.83* | −15.26 ± 2.94** |
| 5 | −3.02 ± 2.51 | −13.56 ± 1.78* | −14.49 ± 2.24* |
| 6 | −2.38 ± 1.82 | −10.08 ± 2.07 | −11.22 ± 2.03 |
| 9 | 0.11 ± 4.30 | −3.26 ± 2.27 | −6.28 ± 4.09 |
| 12 | 1.32 ± 2.70 | 2.65 ± 1.84 | −1.47 ± 2.91 |

Percentage change in IOP = [(IOPnhr − IOP0r)/IOP0h] × 100
Ns—Non-significant, *P < 0.05, P < 0.01, *P < 0.001, ****P < 0.0001; treatment groups were compared with control group, values are expressed as Mean ± SEM From the above results it can be concluded that the IOP reduction achieved from "Brinzolamide ophthalmic solution 0.75% (example-7)" was equivalent with the IOP reduction achieved Azopt® 1.0% Brinzolamide ophthalmic suspension.

We claim:
1. An aqueous ophthalmic solution for treatment of elevated intraocular pressure in patients with ocular hypertension or open-angle glaucoma, the solution comprising
  (a) at least 0.5 w/v % brinzolamide dissolved in the solution;
  (b) at least 1.0 w/v % but no greater than 10.0 w/v % hydroxy-propyl-β-cyclodextrin;
  (c) about 0.2 w/v % to about 5.0 w/v % polyvinyl caprolactam-polyvinyl acetate-polyethylene glycol graft copolymer; and
  (d) water;
    wherein the pH of the solution is about 6.0 to about 7.8 and wherein the ophthalmic solution is free of polysorbate 80.
2. The aqueous ophthalmic solution as in claim 1, wherein the solution comprises of about 0.75 w/v % brinzolamide.
3. The aqueous ophthalmic solution as in claim 1, further comprises isotonizing agent; and a chelating agent.
4. An aqueous ophthalmic solution comprising
  (a) at least 0.5 w/v % brinzolamide but no greater than 0.95 w/v % of brinzolamide dissolved in the solution;
  (b) at least 1.0 w/v % but no greater than 10.0 w/v % hydroxy-propyl-β-cyclodextrin;
  (c) about 0.2 w/v % to about 5.0 w/v % polyvinyl caprolactam-polyvinyl acetate-polyethylene glycol graft copolymer;
  (d) about 0.1 w/v % to about 1.0 w/v % sodium chloride; and
  (e) water;
    wherein the pH of the solution is about 6.0 to about 7.8 and wherein the ophthalmic solution is free of polysorbate 80.
5. The aqueous ophthalmic solution as in claim 4, wherein the solution comprises of about 0.75 w/v % brinzolamide.
6. The aqueous ophthalmic solution as in claim 4, wherein the solution comprises of about 1.0 w/v % polyvinyl caprolactam-polyvinyl acetate-polyethylene glycol graft copolymer.
7. The aqueous ophthalmic solution as in claim 4, wherein the solution comprises of about 5.0 w/v % hydroxy-propyl-β-cyclodextrin.
8. The aqueous ophthalmic solution as in claim 4, wherein the solution comprises of about 0.7 w/v % sodium chloride.
9. The aqueous ophthalmic solution as in claim 4, wherein osmolality of the solution is of about 200 to about 400 mOsm/kg.

10. The method of treating elevated intraocular pressure in patients with ocular hypertension or open-angle glaucoma, the method comprising: topically applying to an eye of the patient at least one drop of the solution of claim 4 to the eye.

\* \* \* \* \*